(12) United States Patent
Essalik et al.

(10) Patent No.: US 6,270,651 B1
(45) Date of Patent: Aug. 7, 2001

(54) GAS COMPONENT SENSOR (76) Inventors: Abetif Essalik, 1677, Chemin du Fleuve, St-Romauld (PQ) (CA), G6W 1Z6; John F. Currie, 6523 Fallwind La., Bethesda, MD (US) 20817-4941

( * ) Notice: Subject to any disclaimer, the term of this patent is extended or adjusted under 35 U.S.C. 154(b) by 0 days.

(21) Appl. No.: 09/498,211

(22) Filed: Feb. 4, 2000

(51) Int. Cl.[7] .................................................. G01N 27/407
(52) U.S. Cl. ......................... 205/784; 205/785; 204/424; 252/62.2
(58) Field of Search .................................. 204/424–429; 205/785, 783.5, 784, 784.5; 252/62.2; 429/30, 33

(56) References Cited

U.S. PATENT DOCUMENTS

| | | |
|---|---|---|
| 4,388,155 | 6/1983 | Chamberland et al. . |
| 4,715,944 * | 12/1987 | Iwamoto et al. ................. 429/191 |
| 5,589,296 * | 12/1996 | Iwamoto et al. ................. 429/191 |
| 5,755,940 * | 5/1998 | Shindo .............................. 204/424 |
| 5,759,366 * | 6/1998 | Ottlinger et al. ................ 204/424 |
| 5,910,239 * | 6/1999 | Maier et al. ..................... 205/781 |
| 5,942,345 * | 8/1999 | Kaun et al. ........................ 429/16 |
| 5,993,624 * | 11/1999 | Matsubara et al. .............. 204/424 |

FOREIGN PATENT DOCUMENTS 91113350.2    2/1992   (EP) .

OTHER PUBLICATIONS

Lang et al. "Material characterization of sputtered sodium–ion conductive ceramics for a prototype CO2 micro–sensor." Sensors and Actuators B 31 pp. 9–12, 1996 month N/A.*

Dubbe et al. "Electrode Kinetic Study of Silver–Ion Doping Effect in Solid–Electrolyte Potentiometric Carbon Dioxide Gas Sensor", J. Electrochem. Soc. 144, pp. 943–947, 1997 month N/A.*

Minami, J. Am. Ceram. Soc., 60, p. 476 (figure 1 only), 1977 month N/A.*

Essalik et al. (Study of a new solid electrolyte thin film micropotentiometric carbon dioxide gas sensor, J. New Mat. Electrochemical Systems 1, 67–70 (1998)), month N/A.

* cited by examiner

*Primary Examiner*—Robert J. Warden, Sr.
*Assistant Examiner*—Kaj K. Olsen (57) ABSTRACT

The present invention is an electrolyte composition in bulk, thick film and sputtered thin film form forming with different metal sensing and reference electrodes a highly stable gas component concentration sensor.

25 Claims, 5 Drawing Sheets

GAS COMPONENT SENSOR

BACKGROUND OF THE INVENTION

The present invention relates to gas component sensors.

Prior art electrochemical sensors for carbon dioxide have disclosed the following useful relationship. As disclosed in "Study of a new solid electrolyte thin film based micropotentiometric carbon dioxide gas sensor" (A. Essalik et al., J. New Mat. Electrochem. Systems 1, p.67–70 (1998)) electrode reactions giving the EMF of such a sensor are as follows:

sensing electrode:

$$\tfrac{1}{2}O_2 + 2e^- + 2Na^+ <=> Na_2O$$

$$CO_2 + Na_2O <=> Na_2CO_3$$

reference electrode:

$$Ag <=> Ag^+ + 1e^-$$

where $Na^+$ and $Ag^+$ are the mobile ions and $Na_2O$ and $Na_2CO_3$ are in solid state. The cell EMF can be written according to the Nernst equation as:

$$EMF = K - [(2.3RT\ Log\ a_{Ag+})/F] - [(2.3RT\ LogP_{O_2})/4F] - [(2.3RT\ Log\ P_{CO_2})/2F]$$

where K is a constant, F and R are the Faraday and gas constants respectively and T is the temperature. According to this equation, at constant $P_{o2}$ and silver-ion activity $a_{Ag}^+$, the EMF depends only on the $CO_2$ partial pressure.

Also disclosed therein is an inherent restriction on the usefulness of that prior art electrode. "However, for practical use, stability of the sensors should be improved." (Essalik et al, p. 70) and the article explained that the sensor lasted only a few hours at operating temperature. This limitation is a common problem of prior art electrolyte based carbon dioxide sensors. Typically, in other prior art carbon dioxide sensors, high temperature operation (400–500° C.) has been required, although the Essalik et al sensor displayed superior operational response at about 250° C.

There is a need for a carbon dioxide sensor after the Essalik et al device for which stable operation is maintained over a long period of time, sufficiently long for application to control or sensing systems wherein low power, low temperature carbon dioxide sensing may used to advantage.

SUMMARY OF THE INVENTION

The present invention is an electrolyte composition. The electrolyte composition in bulk, thick or thin film embodiments are capable of forming with different-metal sensing and reference electrodes a highly stable carbon dioxide sensor. The sensor of Essalik et al. is improved with changed electrolyte composition thereby improving the chemical, mechanical and physical stability of the sensor and at the same time preserving its operational characteristics. The novel electrolyte has: (1) excellent chemical stability and thermal compatibility as to the electrodes and to the preferred ceramic substrates, (2) excellent chemical stability with the environment as to the reference and sensing electrodes, which need not be sealed against the atmosphere to be sensed, (3) effective adherence to the substrate and electrode metals. The novel electrolyte has solved the stability problems of the Essalik et al. sensor.

The invention electrolyte comprises a relatively small amount of reference electrode metal halide and optionally an alkaline. The invention sensor comprises an electrochemically effective amount of the electrolyte in electrochemical connection with sensing and reference electrodes, whereby the sensing and reference electrodes are of different metals.

The invention electrolyte has been additionally found to be reactive with the following species at high concentration: $NO_x$, $SO_x$, chlorine and its ion, fluorine and its ion and bromine and its ion. Although insensitive and non-reactive with carbon monoxide, carbon monoxide gas concentration may be determined from the equilibrium between CO and $CO_2$ when a catalyst is used to enhance the $CO_2$ formation.

In one embodiment of the invention sensor, a hydrophobic layer filter substantially excludes water from the sensed gas reaching the sensor. Other filters are effective in selecting out or permitting in some chemical species such as water carbon monoxide, and oxides of nitrogen and sulfur. Where such filters are effectively used, separate invention sensors may be used as an array to determine a profile of multiple gas components in a sensed gas, thereby providing a process determination to recording, control and/or display means. For example, such a profile for a gas composition as air after combustion with oxidizeable components and compared with a prior air composition will indicate the presence of a fire both with and without flame and smoke or other undesirable condition. Increased carbon dioxide, oxides of sulfur and nitrogen and carbon monoxide in air typically indicate high temperatures and combustion products.

In a further development of the concept of the preceding paragraph, several selectively permeable membranes are currently available and in the prior art that selectively permit passage of gas components while excluding others, as the above example of water exclusion illustrates. An important improvement of the present invention will be to provide one or more of either prior art and/or invention sensors for detection of carbon dioxide, carbon monoxide, and oxides of nitrogen and sulfur with a gas to be sensed after passage through one of such selectively permeable membranes. The present invention provides that a profile of gases sensed at one or more sensors may be indicative of a fire or other alarm or hazard condition may be passed through a selectively permeable membrane to exclude from a sensed gas one or more or the gas components, most preferably components that could interfere with the particular sensor used to sense a gas component for such a profile. The selectively permeable membrane, for example, may exclude oxides of nitrogen to the sensor array or single sensor where the sensor array or single sensor comprises a sensor for oxides of sulfur. An example of a commercially available source of such selectively permeable membranes is from the disclosure of U.S. Pat. Nos. 5,073,176 and 5,922,104, which are incorporated herein, wherein are disclosed several classes of selectively permeable membranes appropriate for use in the present embodiment.

The composite membrane used in this invention as a moisture barrier can be made by mixing any chemical stable solid with any chemical stable hydrophobic polymer. A preferred moisture barrier membrane comprises polyfluorocarbon polymers. These polyfluorocarbon polymers include at least the following: polytetrafluoroethylene, polyvinylidine fluoride, polychlorotrifluoroethylene, polyvinyl fluoride, and perfluoro(alkyl vinyl ethers).

In a preferred embodiment of the invention sensor, thin layer sensing and reference electrodes are in effective connection through the invention electrolyte, the assembly adhered to a top side of a thin ceramic layer also comprising a resistive temperature detector (RTD), whereby a heating layer is adhered to a bottom side of the thin ceramic layer. As described above, a change in the gas concentration of the sensed component changes the EMF across the electrodes, thereby permitting direct or indirect calculation of the concentration of the sensed component. The invention sensor in this embodiment is inexpensive, easy to fabricate, compact, operates at low temperature, and uses very low power. The small size and low power use of the invention sensor enable the skilled person to now use a stable carbon dioxide sensor in low power and temperature sensitive assemblies. The invention sensor has a broad operating range as to carbon dioxide, typically up to and exceeding 10,000 ppm. Such a range of operation allows use of the invention sensor in devices for sensing, recording or controlling air quality, fire detection, chemical, biochemical and biological (including medical) processes, agricultural processes and the like. The present sensor senses a sensed component independent of the flow rate of the component across the sensor. The present sensor eliminates gas tight sealing of at least one electrodes against a sensed or reference gas. The present sensor now permits stable operation through a substantially equilibrium reaction at the electrolyte/reference metal interface of the following reaction:

[Reference electrode metal]$\Leftrightarrow$[Reference electrode metal]$^{z+}$+ze$^{-}$ The above benefits were not realized or taught in the prior art with respect to the novel electrolyte composition of the invention. The invention electrolyte comprises electrochemically effective amounts of one or more alkali metal carbonates, one or more alkaline earth metal carbonates, one or more reference electrode metal halogens with and without doping and optionally an amount of one or more alkali halogens. Although not specifically described herein, the invention electrolyte may comprise substantially electrochemically neutral components while still achieving the objects of the invention. Thus, a description of the invention electrolyte will include a composition with such substantially neutral components so long as the invention benefits are obtained with an electrochemically effective amount of the electrolyte applied across the electrodes of the invention sensor.

The invention electrolyte also comprises a method for conversion from a carbon dioxide sensing electrode to an electrode capable of sensing oxides of nitrogen or sulfur or hydrogen sulfide. At operating temperature, the invention electrode is exposed to substantial amounts of oxides of nitrogen or sulfur or hydrogen sulfide, resulting in reaction of a portion of that component with the invention $CO_2$ electrolyte. The resulting electrolyte (such as including sodium or barium nitrate or sulfate) thereby becomes sensitized to that component in addition to some sensitivity to carbon dioxide. Calculation of the concentrations of the sensed components is possible from a previously determined potential range of component concentrations for carbon dioxide and the other component, or a filter may be arranged such that substantially all carbon dioxide is excluded from the sensed gas.

DETAILED DESCRIPTION OF THE INVENTION

The invention electrolyte comprises the following specific ranges of electrochemically effective components relative to each other in weight percent:

alkali metal carbonate(s): from about 20% to about 99%;

alkaline earth metal carbonate(s): from about 20% to about 99%;

reference electrode metal halogen(s) with and without doping: from an electrochemically effective amount, but most preferably from about 0.5% to 10%; and alkali halogen(s) (optional): about 0.5% to 1.0%.

Exemplary alkali metal carbonates are $Na_2CO_3$, $Li_2CO_3$, $K_2CO_3$, and $Rb_2CO_3$. Exemplary alkaline earth metal carbonates are $BaCO_3$, $CaCO_3$, and $SrCO_3$. Exemplary reference electrode metal halogens with and without doping comprise any inorganic salt of the reference electrode metal such as metal halides or metal oxyanions. Exemplary alkali halogens are NaX, LiX, KX, and RbX where X is chosen from the the following: Cl$^-$, Br$^-$ or I$^-$.

Sensing and reference electrode metals are preferably chosen from the following metals: Ru, Rh, Pd, Re, Os, Ir, Pt, Au, or Ag. It does not matter which two of the preferred metals are chosen from among this group for the sensing and reference electrode so long as the two metals are different. Optimizing price and ease in fabrication will result in a choice from the above group of sensing and reference electrodes.

For a thin film embodiment of the present invention, it has been found that a ceramic substrate of alumina (monocrystalline or polycrystalline) is a preferred material, although many other appropriate supports are appropriate depending on adhesion and heat transfer characteristics of the substrate. A preferred thickness of the ceramic substrate is from about 50 μm to less than about 1 millimeter. It is preferred to prepare the surfaces for thin film deposition by cleaning in baths of warm acidic solution (such as Citronox), warm acetone solution, warm isopropanol solution, and warm deionized water dried in nitrogen gas at about 140° C.

Figure 1:
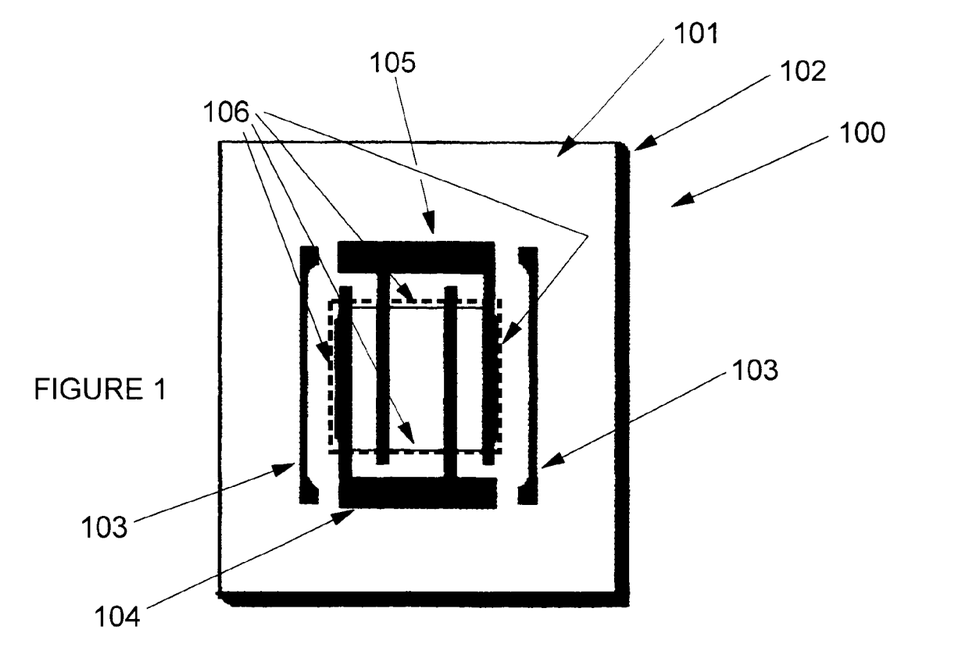
FIG. 1 is a top view of the interdigitated reference and sensing electrodes and RTD's on a top side of a thin support layer, with the outline of the invention electrolyte shown in broken lines
Figure 2:
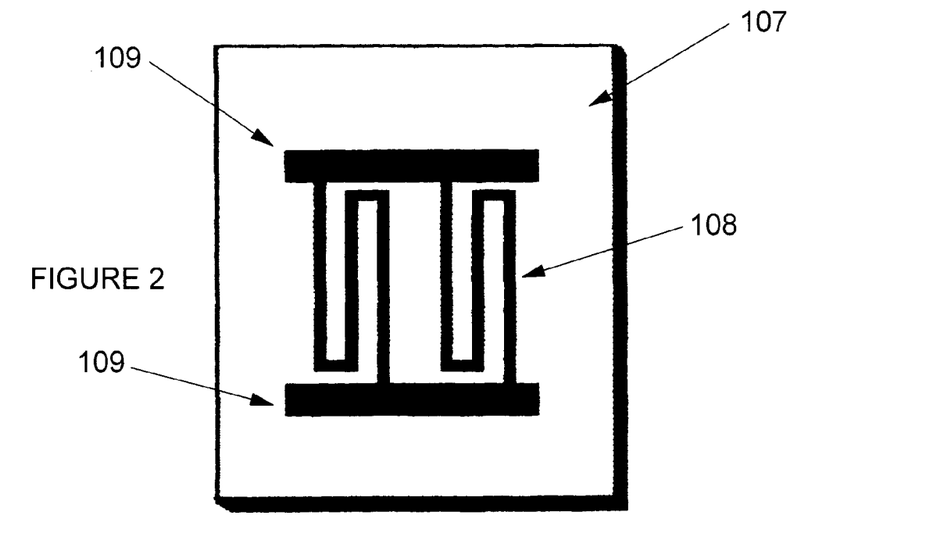
FIG. 2 is a bottom view of a bottom side of the thin support layer, having adhered thereon a resistive heating element.

FIGS. 1 and 2 show a thin film invention sensor assembly 100 having ceramic substrate with a top side 101, thickness 102 and bottom side 107. Sensing electrode 104 is interdigitated with reference electrode 105 between RTD's 103, all of which are applied as thin films to top side 101 via sequential e-beam evaporation and patterned by lift-off. When using Au or Pt for sensitive electrode or otherwise depositing such on the substrate, it is preferable to first deposit a layer of chromium to improve adherence of the thin layer metals. It is preferred that electrode layers have the following thicknesses: Ag/>15000 Angstroms; Pt—Cr/ >1000 Angstroms; Au—Cr/>5000 Angstroms.

The RTD's are preferably Pt, as well as the thin film heater 108 having wire connections 109. It is apparent to the skilled person that the embodiment of FIGS. 1 and 2 comprise sites for wire lead attachment for connection to electrodes 104 and 105, RTD's 103 and heater 108. The outline 106 of FIGS. 1 and 2 shows the preferred extent of deposited invention electrolyte on assembly 100, thereby covering a substantial portion of the interdigits of electrodes 104 and 105.

The following is an example process: after deposition of the electrodes 104 and 105, electrolyte 106 is deposited in the following manner. A sputter target disk is prepared from the powder of the invention electrolyte. The disk is prepared similarly to the process of Essalik et al. by hydraulic and cold isostatic press. The target is mounted in the RF magnetron sputtering guns in a UHV chamber for low pressure chemical vapor deposition to the thin film. The target is hygroscopic and therefore is maintained in vacuum protected by load lock. The sputtering chamber of the RF magnetron is back-filled with pure argon to a working pressure. Sputtering of the target to the substrate produces a thin film of more than 20,000 Angstroms. The outline of the deposited electrolyte is maintained only such that it is substantially electrochemically in touch with opposing edges of the interdigits of electrodes 104 and 105.

The following list are actual examples sputtering target disk compositions for four embodiments of the invention electrolyte incorporated into a $CO_2$ sensor assembly 100 and having $CO_2$ sensing capabilities according to the performance characteristics described herein:

1. BaCO3, 17.7615 g.; $Na_2CO_3$, 5.2995; AgCl, 0.3583 g.; NaCl, 0.0055 g. or 0.0 g.
2. $BaCO_3$, 17.7615 g.; $Na_2CO_3$, 5.2995; AgI, 0.5869 g.; NaI, 0.0055 g. or 0.0 g.
3. $BaCO_3$, 17.7615 g.; $Li_2CO_3$, 5.2995; AgCl, 0.3583 g.; NaCl, 0.0055 g. or 0.0 g.
4. $BaCO_3$, 17.7615 g.; $Li_2CO_3$, 5.2995; AgI, 0.3583 g.; NaI, 0.0055 g. or 0.0 g.

Figure 3:
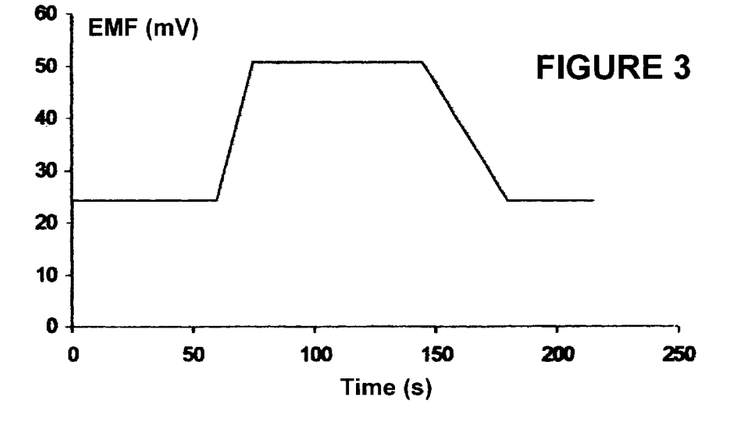
FIG. 3 is a graph of the EMF response of the invention thin film electrolyte to $CO_2$ in a sensed gas.

FIGS. 3–8 show performance characteristics of the sensor assembly 100 wherein heater 108 causes the electrolyte 106 to reach about 250° C. and a higher concentration $CO_2$ containing gas is introduced to and withdrawn from the electrolyte 106 surface. For a single, exemplary sensed gas, FIG. 3 shows that full response time to the higher concentration $CO_2$ containing gas requires only about 20 seconds (from about 65 seconds to 85 seconds) to reach accurate measurement and about 65 seconds to recover once the higher concentration $CO_2$ gas was replaced with the previous gas. In general, the thin film embodiments of assembly 100 comprise sensors for $CO_2$, $NO_2$ and $SO_2$. The results for $CO_2$ sensor assembly 100 at 250° C. were about 45.3 mV/decade sensitivity, 10–30 seconds for response time and around 60 seconds recovery time. The results for $NO_2$ sensor assembly 100 at 250° C. were about 48.3 sensitivity, 2–10 seconds for response time and around 10 seconds recovery time. The results for $SO_2$ sensor assembly 100 at 250° C. were about 50.3 mV/decade sensitivity, 1–2 seconds for response time and around 5 seconds recovery time. Exemplary electrolyte compositions for $NO_2$ and $SO_2$ sensor assemblies are respectively: (1) $BaNO_3$, AgCl or AgI, and NaCl or NaI and (2) $BaSO_4$, $Na_2SO_4$, AgCl or AgI, $V_2O_5$ and NaCl or NaI. Sputtering target and thin film deposition techniques for $NO_2$ and $SO_2$ sensor assemblies are as above.

Figure 4:
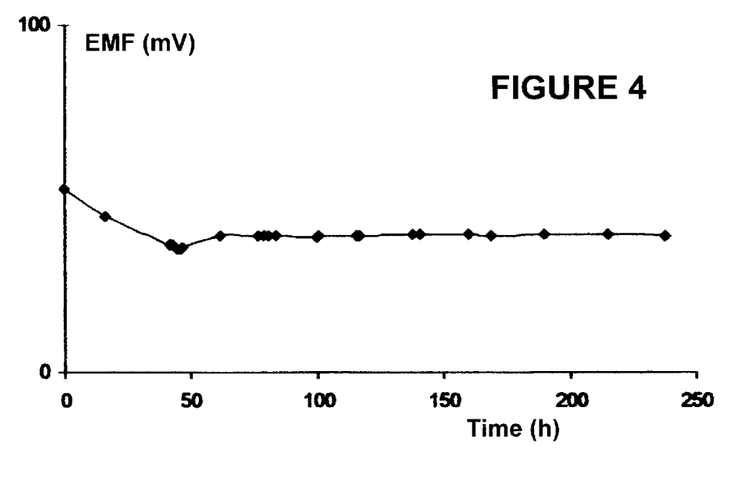
FIG. 4 is a graph demonstrating stability of the invention $CO_2$ sensor.

FIG. 4 is a graph demonstrating stability of the invention $CO_2$ sensor. It easily seen that sensor response is substantially flat after an initial period of decline.

Figure 5:
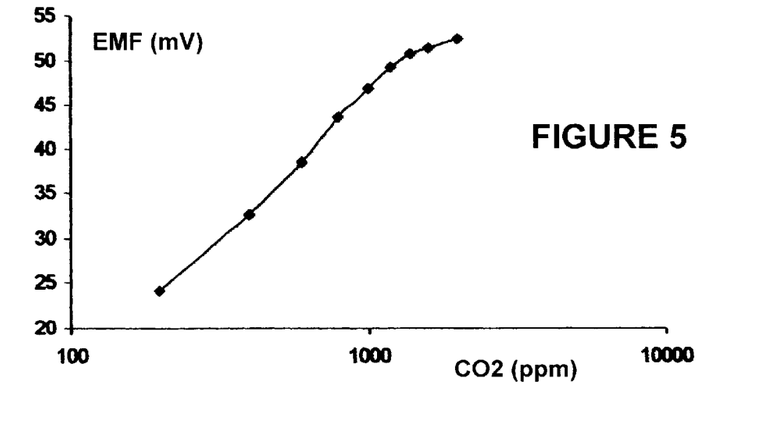
FIG. 5 is a graph demonstrating the response of the invention $CO_2$ sensor to $CO_2$ levels in a gas.

FIG. 5 is a graph demonstrating the response of the invention $CO_2$ sensor to $CO_2$ levels in a gas. The lower $CO_2$ concentration sensitivity at about 2000 ppm and below is especially useful for devices incorporating the $CO_2$ sensor into a display, recording or control system where the gas will come into contact with breathing air of animal life.

Figure 6:
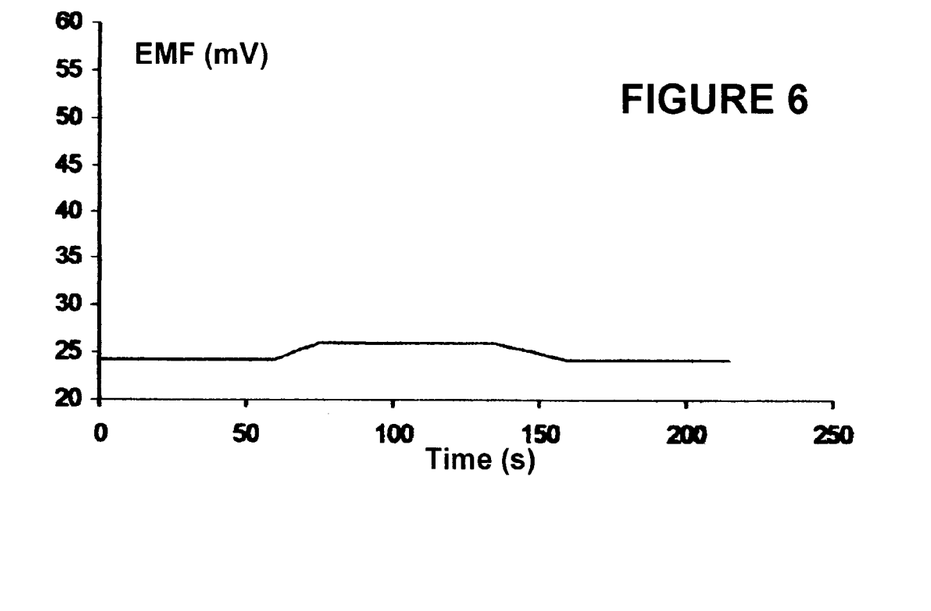
FIG. 6 is a graph of the invention $CO_2$ sensor response to non-$CO_2$ components of air as to the response of the sensor shown in FIG. 5. 1. from 0s to 60s: response of the sensor to 200 ppm $CO_2$ in air, 2. from 60 to 160s response of the sensor to 200 ppm $CO_2$ in air in the presence of 10 ppm $NO_2$, and 3. from 160 to 220s response of the sensor to 200 ppm $CO_2$ in air in the presence of 20 ppm $SO_2$.

FIG. 6 is a graph of the invention $CO_2$ sensor response to non-$CO_2$ components of air as to the response of the sensor shown in FIG. 5.

Figure 7:
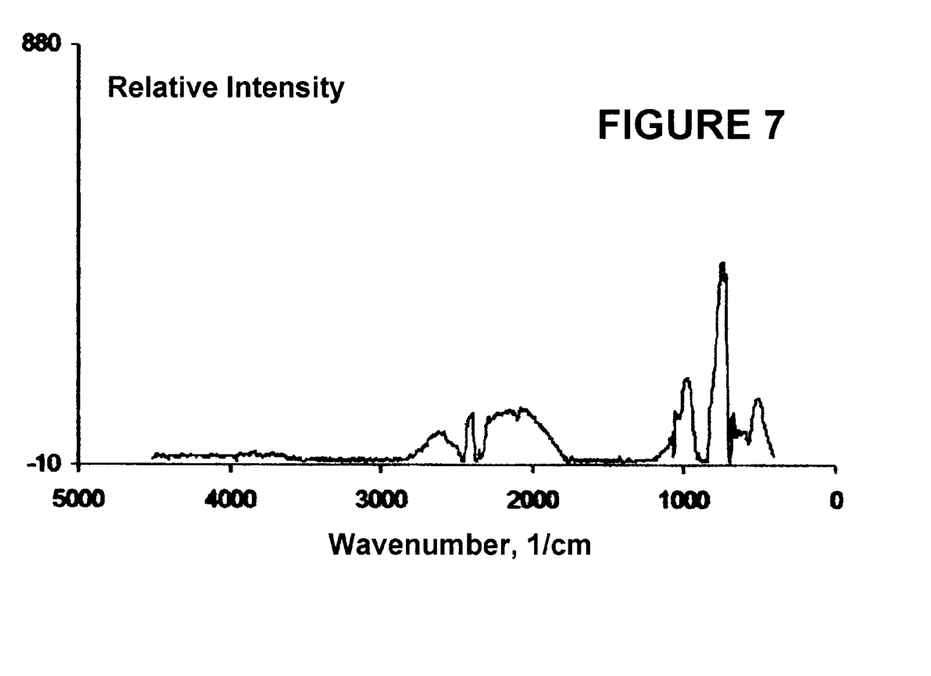
FIG. 7 is an infrared spectra of the bulk invention electrolyte.

FIG. 7 is an infrared spectra of the powder of the invention electrolyte.

Figure 8:
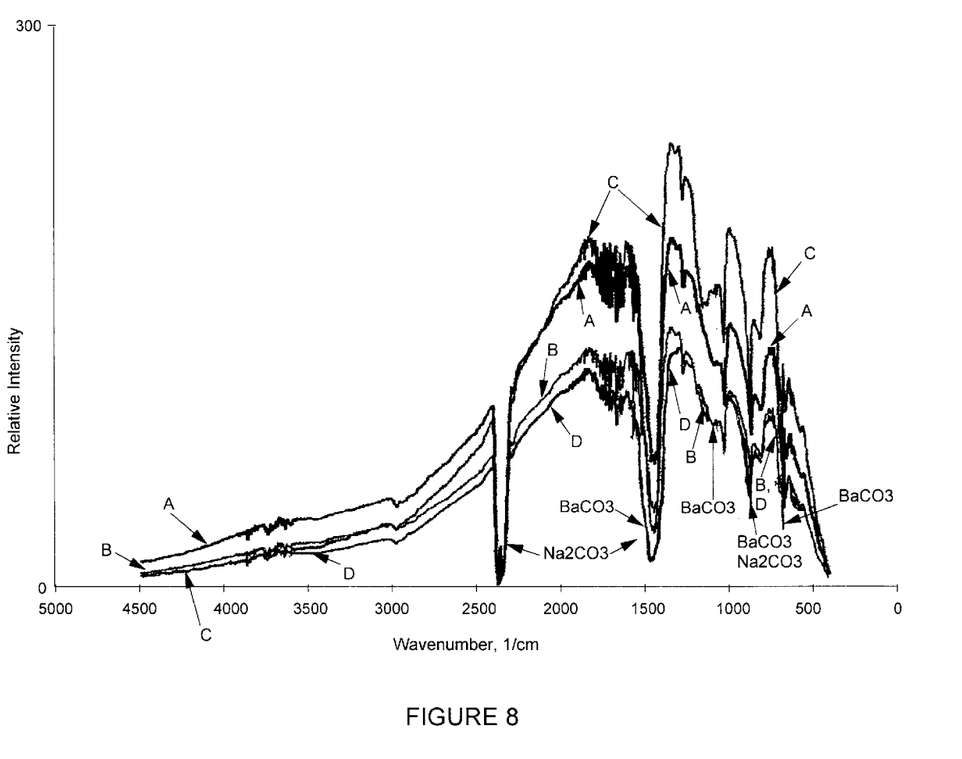
FIG. 8 shows the infrared spectra of the bulk and thin film invention electrolyte maintained at 130° C. and 400° C. for 14 days, demonstrating component integrity and continued stability of the invention electrolyte over time.
Figure 9:
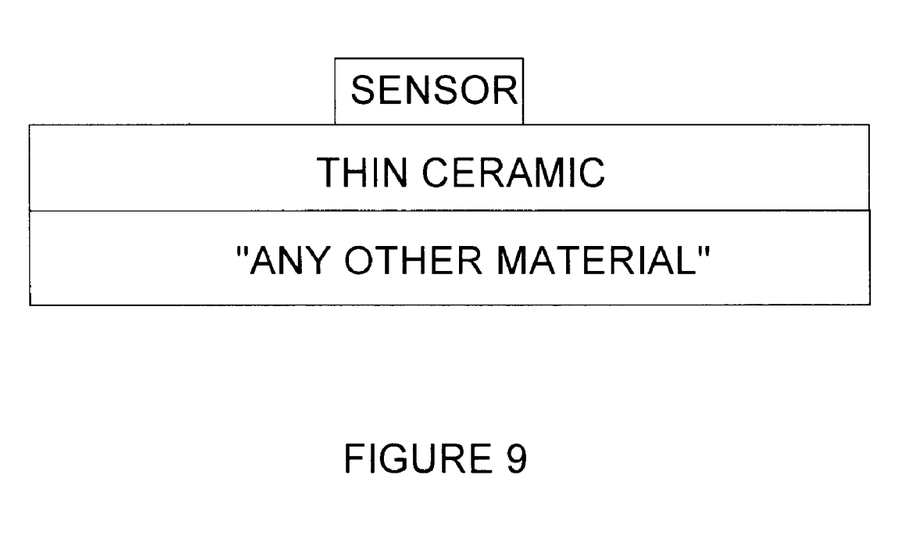
FIG. 9 is a generalized side view of the invention sensor affixed to an underlying ceramic layer which may also affixed to any other appropriate material as a support to the ceramic material.

FIG. 8 are the infrared spectra of the powder and thin film invention electrolyte maintained at 130° C. and 400° C. for 14 days, demonstrating component integrity and continued stability of the invention electrolyte over time. Component locations on the spectrum are shown in the Figure. Traces A and C show, respectively, powder composition after 14 days of exposure to heating in air at 400° C. and 130° C. Traces B and D show, respectively, thin film composition after 14 days of exposure to heating in air at 130° C. and 400° C. The thin film embodiment of the invention electrolyte remains effective in composition through long periods of exposure to much higher temperatures than required for effective operation.

The specific example of the above thin film $CO_2$ sensor operates effectively with a heating power of about 500 mW. The low power usage translates into low ambient heat transfer, thereby permitting use in compact, temperature sensitive devices. It is, however, an alternate embodiment of the sensor assembly to do without the RTD's and thin film heater where ambient conditions of a sensed gas are within the temperature range required by the invention sensor assembly.

The above design disclosures present the skilled person with considerable and wide ranges from which to choose appropriate obvious modifications for the above examples. However, the objects of the present invention will still be obtained by the skilled person applying such design disclosures in an appropriate manner.

We claim:

1. An electrolyte composition effective for sensing a gas concentration of carbon dioxide comprising electrochemically effective concentrations of:
   (a) one or more alkali metal carbonates;
   (b) one or more alkaline earth metal carbonates; and
   (c) one or more reference electrode metal halogens, where a reference electrode metal is chosen from the group consisting of ruthenium, rhodium, palladium, rhenium, osmium, iridium, platinum and gold and the halogens of the reference metal halogens are chlorine, bromine or iodine.

2. The composition of claim 1 wherein the composition further comprises an electrochemically effective concentration of one or more alkali halogens, whereby the halogens of the alkali halogens are chlorine, bromine or iodine.

3. The composition of claim 1 wherein the concentration of alkali metal carbonates is greater than about 20 weight percent of the total weight of alkali metal carbonates, alkaline earth metal carbonates, and reference electrode metal halogens.

4. The composition of claim 1 wherein the concentration of alkaline earth metal carbonates is greater than about 20 weight percent of the total weight of alkali metal carbonates, alkaline earth metal carbonates, and reference electrode metal halogens.

5. The composition of claim 1 wherein the concentration of reference electrode metal halogens is greater than about 0.5 weight percent of the total weight of alkali metal carbonates, alkaline earth metal carbonates, and reference electrode metal halogens.

6. The composition of claim 1 wherein the composition further comprises a concentration of one or more alkali halogens greater than about 0.5 weight percent of the total weight of alkali metal carbonates, alkaline earth metal carbonates, reference electrode metal halogens and alkali halogens, whereby the halogens of the alkali halogens are chlorine, bromine or iodine.

7. A thin film electrolyte effective for sensing a gas concentration of carbon dioxide comprising electrochemically effective concentrations of (a) one or more alkali metal carbonates in a first composition, (b) one or more alkaline earth metal carbonates in the first composition, (c) one or more reference electrode metal halogens, where a reference metal electrode metal is chosen from the group consisting of ruthenium, rhodium, palladium, rhenium, osmium, iridium, platinum and gold and the halogens of the reference metal halogens are chlorine, bromine or iodine in the first composition; and (d) the first composition deposited in a thin film on a substrate.

8. The electrolyte of claim 7 herein the first composition nfurther comprises an electrochemically effective concentration of one or more alkali halogens, whereby the halogens of the alkali halogens are chlorine, bromine or iodine.

9. The composition of claim 7 wherein the concentration of alkali metal carbonates is greater than about 20 weight percent of the total weight of alkali metal carbonates, alkaline earth metal carbonates, and reference electrode metal halogens.

10. The composition of claim 7 wherein the concentration of alkaline earth metal carbonates is greater than about 20 weight percent of the total weight of alkali metal carbonates, alkaline earth metal carbonates, and reference electrode metal halogens.

11. The composition of claim 7 wherein the concentration of reference electrode metal halogens with and without doping is greater than about 0.5 weight percent of the total weight of alkali metal carbonates, alkaline earth metal carbonates, and reference metal halogens.

12. The composition of claim 7 wherein the composition further comprises a concentration of one or more alkali halogens greater than about 0.5 weight percent of the total weight of alkali metal carbonates, alkaline earth metal carbonates, reference electrode metal halogens and alkali halogens, whereby the halogens of the alkali halogens are chlorine, bromine or iodine.

13. A carbon dioxide sensor assembly comprising:

(a) an electrolyte comprising electrochemically effective concentrations of:
(i) one or more alkali metal carbonates;
(ii) one or more alkaline earth metal carbonates; and
(iii) one or more reference electrode metal halogens, wherein the reference electrode metal of the reference electrode metal halogens is chosen from the group consisting of Ru, Rh, Pd, Re, Os, Ir, Pt, Au, and Ag, whereby the halogens of the reference electrode metal halogens are chlorine, bromine or iodine;

(b) the electrolyte in electrochemical connection between a sensing electrode and a reference electrode, whereby the reference electrode consists of a first reference electrode metal and the sensing electrode consists of any other reference electrode metal; and (c) the electrolyte and electrodes are supported on a substrate.

14. The assembly of claim 13 wherein the electrolyte further comprises an electrochemically effective concentration of one or more alkali halogens, whereby the halogens of the alkali halogens are chlorine, bromine or iodine.

15. The composition of claim 13 wherein the concentration of alkali metal carbonates is greater than about 20 weight percent of the total weight of alkali metal carbonates, alkaline earth metal carbonates, and reference electrode metal halogens.

16. The assembly of claim 13 wherein the concentration of alkaline earth metal carbonates is greater than about 20 weight percent of the total weight of alkali metal carbonates, alkaline earth metal carbonates, and reference electrode metal halogens.

17. The assembly of claim 13 wherein the concentration of reference electrode metal halogens with and without doping is greater than about 0.005 weight percent of total weight of alkali metal carbonates, alkaline earth metal carbonates, and reference electrode metal halogens.

18. The assembly of claim 13 wherein the composition further comprises a concentration of one or more alkali halogens greater than about 0.5 weight percent of the total weight of alkali metal carbonates, alkaline earth metal carbonates, reference electrode metal halogens and alkali halogens, whereby the halogens of the alkali halogens are chlorine, bromine or iodine.

19. The assembly of claim 13 wherein the substrate comprises a thin layer having adhered to a top side the electrolyte, the electrodes and a reference temperature detector and on a bottom side a thin layer heater adapted to raise the temperature of the electrolyte to an operating temperature.

20. The assembly of claim 13 wherein the substrate comprises a thin layer having adhered to a top side the electrolyte, the electrodes and a reference temperature detector and on the top side a thin layer heater adapted to raise the temperature of the electrolyte to an operating temperature.

21. The assembly of claim 13 wherein the electrolyte further comprises an electrochemically effective concentration of one or more alkali halogens, whereby the halogens of the alkali halogens are chlorine, bromine or iodine.

22. A carbon dioxide sensor assembly comprising:

(a) an electrolyte comprising electrochemically effective concentrations of:
(i) one or more alkali metal carbonates;
(ii) one or more alkaline earth metal carbonates; and
(iii) one or more reference electrode metal halogens, wherein the reference electrode metal of the reference electrode metal halogens is chosen from the group consisting of Ru, Rh, Pd, Re, Os, Ir, Pt, Au, and Ag, whereby the halogens of the reference electrode metal halogens are chlorine, bromine or iodine;

(b) the electrolyte in electrochemical connection between a sensing electrode and a reference electrode, whereby the reference electrode consists of a first reference electode metal and the sensing electrode consists of any other reference electrode metal;

(c) the electrolyte and electrodes are deposited as a thin film and supported on a substrate whereupon the electrodes are in contact with a same first gas to be sensed by the sensor; and (d) electrical connection of the electrodes, such that a voltage across the electrodes is capable of being measured, whereby the measured voltage indicates concentration of carbon dioxide in the first gas.

23. A method for determining carbon dioxide concentration in a first gas comprising:

(a) providing a carbon dioxide sensor assembly comprising an electrolyte comprising electrochemically effective concentrations of:
 (i) one or more alkali metal carbonates;
 (ii) one or more alkaline earth metal carbonates; and
 (iii) one or more reference electrode metal halogens, where a reference electrode metal is chosen from the group consisting of ruthenium, rhodium, palladium, rhenium, osmium, iridium, platinum and gold and the halogens of the reference metal halogens are chlorine, bromine or iodine;

(b) the assembly further comprising the electrolyte in electrochemical connection between a sensing electrode and a reference electrode, whereby the reference electrode consists of a first reference electrode metal and the sensing electrode consists of any other reference electrode metal;

(c) the assembly further comprising the electrolyte and electrodes are deposited as a thin film and supported on a substrate whereupon the electrodes are in contact with the same first gas to be sensed by the sensor;

(d) the assembly further comprising a means for measuring a voltage across the electrodes and for calculation of a concentration of carbon dioxide in the first gas; and (e) operating the sensor so that the electrolyte is maintained at about 250 degrees Celsius or above and a carbon dioxide containing gas contacts the electrolyte and the electrodes such that a voltage across the electrodes indicates concentration of carbon dioxide in the first gas.

24. The method of claim 23 wherein the electrolyte further comprises an electrochemically effective concentration of one or more alkali halogens, whereby the halogens of the alkali halogens are chlorine, bromine or iodine.

25. The method of claim 23 wherein the electrolyte is maintained at substantially below about 400° C.

* * * * *